(12) United States Patent
Japrung et al.

(10) Patent No.: US 9,834,772 B2
(45) Date of Patent: Dec. 5, 2017

(54) APTAMERS BOUND HUMAN SERUM ALBUMIN AND GLYCATED HUMAN SERUM ALBUMIN

(71) Applicant: NATIONAL SCIENCE AND TECHNOLOGY DEVELOPMENT AGENCY, Pathumthani (TH)

(72) Inventors: Deanpen Japrung, Pathumthani (TH); Tararaj Dharakul, Pathumthani (TH); Suchintana Chumseng, Pathumthani (TH)

(73) Assignee: National Science & Technology Development Agency, Pathumthani (TH)

( * ) Notice: Subject to any disclaimer, the term of this patent is extended or adjusted under 35 U.S.C. 154(b) by 0 days.

(21) Appl. No.: 15/027,970

(22) PCT Filed: Oct. 15, 2014

(86) PCT No.: PCT/TH2014/000048
§ 371 (c)(1),
(2) Date: Apr. 7, 2016

(87) PCT Pub. No.: WO2015/057177
PCT Pub. Date: Apr. 23, 2015

(65) Prior Publication Data
US 2016/0237436 A1 Aug. 18, 2016

(30) Foreign Application Priority Data

Oct. 17, 2013 (TH) .................. 1301005956

(51) Int. Cl.
*C12N 15/11* (2006.01)
*C12N 15/115* (2010.01)

(52) U.S. Cl.
CPC ........ *C12N 15/115* (2013.01); *C12N 2310/16* (2013.01); *C12N 2310/3517* (2013.01)

(58) Field of Classification Search
None
See application file for complete search history.

(56) References Cited

U.S. PATENT DOCUMENTS

| 5,518,720 A | 5/1996 | Cohen | |
|---|---|---|---|
| 2009/0023672 A1 | 1/2009 | Inoue et al. | |
| 2009/0042237 A1 * | 2/2009 | Smith | G01N 21/31 435/29 |
| 2011/0318846 A1 * | 12/2011 | Lee | C07K 14/4737 436/501 |

OTHER PUBLICATIONS

Carter, "Ultramicroestimation of human serum albumin: Binding of the cationic dye, 5,5'-dibromo-o-cresolsulfonphthalein," Microchemical Journal (1970) 15(4):531-539.
Cohen et al., "Measuring glycated proteins: clinical and methodological aspects," Diabetes Technology & Therapeutics (1999) 1(1):57-70.
Doumas et al., "Origins of Dye-Binding Methods for Measuring Serum Albumin," Clinical Chemistry (2009) 55(3):583-584.
Doumas et al., "Serum and urine albumin: a progress report on their measurement and clinical significance," Clinica Chimica Acta (1997) 258(1):3-20.
Ellington et al., "In vitro selection of RNA molecules that bind specific ligands," Nature (1990) 346(6287):818-822.
Fanali et al., "Human serum albumin: from bench to bedside," Mol Aspects Med (2012) 33(3):209-290.
Gustafsson, "Improved specificity of serum albumin determination and estimation of "acute phase reactants" by use of the bromcresol green reaction," Clinical Chemistry (1976) 22(5):616-622.
Higashimoto et al., "In vitro selection of DNA aptamers that block toxic effects of Age on cultured retinal pericytes," Microvascular Research (2007) 74(1):65-69.
Ikeda et al., "Determination of glycated albumin by enzyme-linked boronate immunoassay (ELBIA)," Clinical Chemistry (1998) 44(2):256-263.
Kohzuma et al., "Basic Performance of an Enzymatic Method for Glycated Albumin and Reference Range Determination," J Diabetes Sci Technol (2011) 5(6):1455-1462.
Louderback et al., "A new dye-binding technic using bromcresol purple for determination of albumin in serum," Clinical Chemistry (1968) 14(8):793-794.
Okumura, "Glycated albumin induces activation of activator protein-1 in retinal glial cells," Jpn J Ophthalmol (2007) 51:236-237.
Pinnell et al., "New automated dye-binding method for serum albumin determination with bromcresol purple," Clinical Chemistry (1978) 24(1):80-86.
Rodkey, "Direct Spectrophotometric Determination of Albumin in Human Serum," Clinical Chemistry (1965) 11(4):478-487.
Shaklai et al., "Nonenzymatic glycosylation of human serum albumin alters its conformation and function," J Biol Chem (1984) 259(6):3812-3817.
Shuvaev et al., "Increased protein glycation in cerebrospinal fluid of Alzheimer's disease," Neurobiol Aging (2001) 22(3):397-402.
Song et al., "Aptamers and Their Biological Applications," Sensors (2012) 12(1):612-631.
Sugio et al., "Crystal structure of human serum albumin at 2.5 A resolution," Protein Eng (1999) 12(6):439-446.
Thomas et al., "Interactions between Renin Angiotensin System and Advanced Glycation in the Kidney," J Am Soc Nephrol (2005) 16:2976-2984.

(Continued)

*Primary Examiner* — Kate Poliakova-Georgantas
(74) *Attorney, Agent, or Firm* — Morrison & Foerster LLP

(57) ABSTRACT

This invention is about the selection and development of aptamers that specifically bound HSA and GHSA. HSA and GHSA are associated with diabetes mellitus. The length of selected aptamers are around 46-106 bases, in which aptamers against HSA are consisting of 46-106 bases and aptamers against GHSA are consisting of 49-71 bases. All selected aptamers against HSA and GHSA can be potentially applied for detection and monitoring of diabetes mellitus in combination with blood glucose and HbA1C level. They also can applied in the drug development and drug delivery system in the diabetes mellitus and Alzheimer disease. In addition, chemical or fluorescence labeled these aptamers can be used for study function and location of HSA and GHSA.

14 Claims, 3 Drawing Sheets

(56) References Cited

OTHER PUBLICATIONS

Tuerk et al., "Systematic evolution of ligands by exponential enrichment: RNA ligands to bacteriophage T4 DNA polymerase," Science (1990) 249(4968):505-510.
Webster et al., "A study of the interaction of bromocresol green with isolated serum globulin fractions," Clinica Chimica Acta (1974) 53(1):109-115.
Winocour et al., "A comparison of direct measures of glycaemia and glycated blood proteins in insulin-dependent diabetes mellitus," Clin Biochem (1989) 22(6):457-461.
Worner et al., "Selective determination of non-enzymatic glycosylated serum albumin as a medium term index of diabetic control," Int J Clin Pharmacol Ther Toxicol (1993) 31(5):218-222.
Ziyadeh et al., "Glycated albumin stimulates fibronectin gene expression in glomerular mesangial cells: involvement of the transforming growth factor-beta system," Kidney Int (1998) 53(3):631-638.

\* cited by examiner

G8 aptamer
5'-Biotin-GGTGCGGTTCGTGCGGTTGTAGTACTCGTGGCCGATAGAGGTAGTTTCG-3'
Clone9 aptamer
5'-Biotin-TAACTCACTCCATACTCACTTGCTGATTCGCCAACAACACACCCTTAAACAGTCCC-3'
Fig. 7
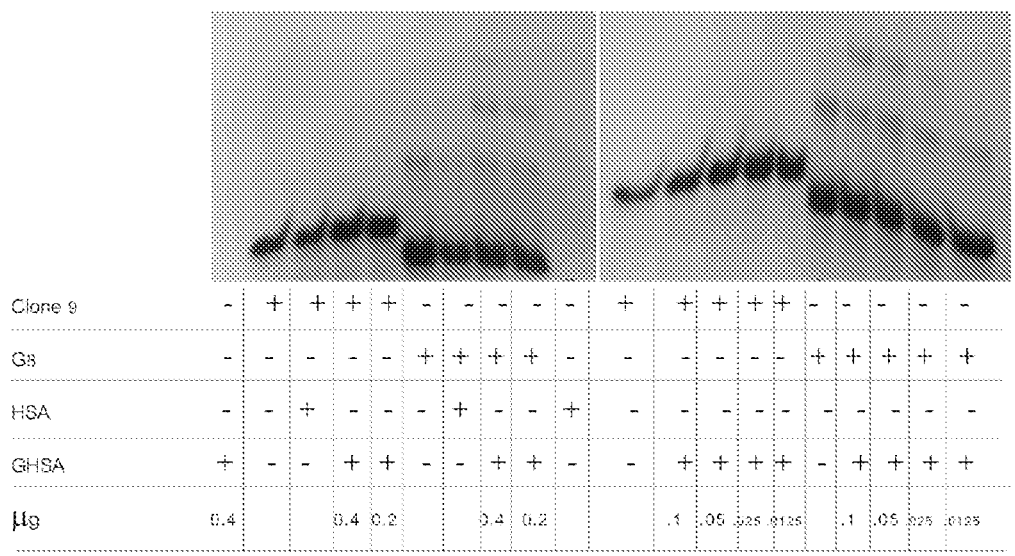
Fig. 8
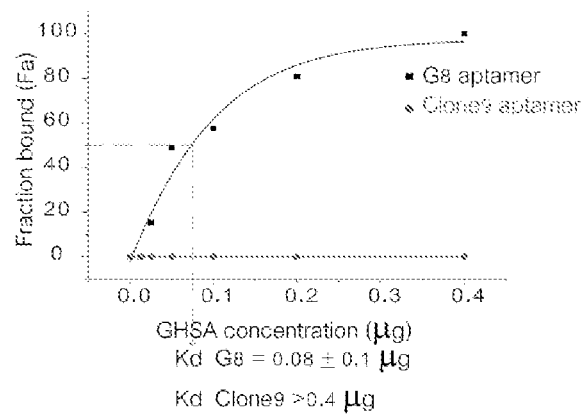
Fig. 9

APTAMERS BOUND HUMAN SERUM ALBUMIN AND GLYCATED HUMAN SERUM ALBUMIN

CROSS-REFERENCE TO RELATED APPLICATIONS

This application is a U.S. National Stage Application of International Application No. PCT/TH2014/000048, filed Oct. 15, 2014, which claims priority to and the benefit of Thailand Patent Application No. 1301005956, filed Oct. 17, 2013. The contents of each of these applications are incorporated herein by reference in their entirety.

INCORPORATION BY REFERENCE OF SEQUENCE LISTING

The present application includes a Sequence Listing in electronic format. The Sequence Listing is provided as a file entitled 584572000800SEQLISTING.TXT, created Dec. 23, 2016 which is 8,993 bytes in size. The information in the electronic format of the Sequence Listing is incorporated by reference in its entirety.

FIELD OF THE INVENTION

The present invention relates to aptamers bound human serum albumin and glycated human serum albumin

BACKGROUND OF THE INVENTION

Human Serum Albumin (HSA) is 66.4 kDa abundant protein in human serum (50% of total protein) composing of 585 amino acids with the heart shape structure (Sugio, *Protein Eng*, Vol. 12, 1999, 439-446). Multifunctional HSA protein is associated with its structure that allowed to bind and transport a number of metabolizes such as fatty acids, metal ions, bilirubin and some drugs (Fanali, *Molecular Aspects of Medicine*, Vol. 33, 2012, 209-290). HSA concentration in serum is around 3.5-5 g/dL. Abnormal HSA level is resulting in abnormal function in human system and can be an indicator for some diseases. The high HSA level can be found in heart failure condition, Alzheimer and diabetes mellitus (Fanali, *Molecular Aspects of Medicine*, Vol. 33, 2012, 209-290).

Glycated human serum albumin (GHSA) is glycation product of HSA protein, in which glucose sugar is non-enzymatically added on some amino acids (Lysine 199, 281, 439 etc.) of the HSA molecule (Fanali, *Molecular Aspects of Medicine*, Vol. 33 2012, 209-290). GHSA can be produced in condition with the high level of sugar concentration, which usually found in diabetes mellitus patients. Adding sugar on the GHSA molecule results in three-dimensional structure changes and interferes normal HSA protein functions, for examples lower binding affinity to bilirubin (up to 50%) and cis-parinaric acid (up to 20 times) (Shaklai, *Journal of Biological Chemistry*, Vol. 259, No. 6, 1984, 3812-3817). Therefore, GHSA level can be an indicator for diabetes mellitus complications and Alzheimer diseases (Shuvae, *Neurobiology of Aging*, Vol. 22, No. 3, 2001, 397-402). In addition, GHSA level is correlated with blood sugar and glycated hemoglobin (HbAlc) and its half-life is shorter than HbAlc, therefore GHSA level can be the better indicator for diabetes mellitus detection and monitoring (Wincour, *Clinical Biochemistry*, Vol. 22, 1989, 457-461, Worner, *International Journal of Pharmacology, Therapy, and Toxicology*, Vol. 31, No. 5, 1993, 218-222).

In case of diabetic nephropathy, GHSA will interact with receptor in the mesangial cells, which are associated with the glomerular dysfunction (Cohen, *Clinical and Methodological Aspects. Diabetes Technology & Therapeutics*, 1999, Thomas, *Journal of* 10 *American Society of Nephrology*, Vol. 16, 2005, 2976-2984, Ziyadeh, *Kidney International*, Vol. 53, 1998, 631-638). In 1994 and 1995, Cohen and colleagues found that monoclonal antibody that specifically bound GHSA could retard the progression of diabetes nephropathy in mice and prevent the GHSA from causing further harm in the kidney (Cohen, U.S. Pat. No. 5,518,720). Therefore this antibody have a potential for drug development in diabetes nephropathy complication.

It has been found that GHSA is associated with the protein phosphorylation in retinal cell growth, resulting in diabetes retinopathy (Okumura, *Journal of Opthalmology*, Vol. 51, 2007, 231-243). In 2007, Higashimoto and his colleagues selected single stranded DNA (ssDNA) that specifically bound to GHSA in vitro and they also found that some selected aptamers could inhibit GHSA toxicity in retinal pericytes (Higashimoto, *Microvascular Research*, Vol. 74, 2007, 65-69, Inou, US patent number US/2009/0023672 A1), which can be developed for the anti-diabetes retinopathy drugs.

Human Serum Albumin Detection

1. Dye-Binding Method: There are 2 types of GHSA detection by dye, Which are Bromcresol Green (BCG) and Bromcresol Purple (BCP).

Bromcresol Green: In 1965, it has been proved that bromcresol green, which is negative charge molecule could bind HSA protein at pH 7-7.1. The absorbance of the binding complex could be detected by spectrophotometry at the absorption wavelength 615 nm. Increasing of HSA concentration is associated with decreasing of 615 nm absorption (Rodkev, *Clinical Chemistry*, Vol. 11, No 4, 1965). In 1976, BCG has been found to bind to other proteins ($\alpha$- and $\beta$-globulin) in condition with the low HSA for examples kidney failure and dialysis patients (Gustafsson, *Clinical Chemistry*, Vol. 22, No. 616, 1976, Webster, *Clinica Chimica Acta*, Vol. 53, No. 109, 1974). Therefore, BCG can be only used for screening method.

Bromcresol Purple: Detection of HSA using BCP method was firstly used in 1970 by Louderback and his colleagues (Louderback, *Clinical Chemistry*, Vol. 14, 1970, 793-794) and future developed by Carter and his colleagues (Carter, *Microchem Journal*, Vol. 15, 1970, 531-539). In 1978, Andrew and colleagues invented automate system based on BCP method (Andrew *Clin Chem*, Vol. 24., No. 1, 1978, 80-86). The principle of BCP method is based on BCP charge, which is the higher positive charge dye than the BCG charge. The BCP can specifically bind to HSA, leading to more broaden absorption wavelength comparing with BCG method. In addition, BCP method can be used for detection of human serum albumin in the lower concentration. Therefore, BCP method is more popular method than BCG method. However, it has been reported that 3-carboxy-4-methyl-5-propyl-2-furanpropanoic acid (CMPF), which can be found in kidney failure patients who have been done dialysis for a long period of time, interferes BCP method (Basil *Clinical Chemistry*, Vol. 55, No. 3, 2009, 583-584). Therefore, it is better to develop new method for HSA measurement that can be used in kidney failure patients and other abnormal conditions.

2. Immunochemical Assay: Immunochemical assay seems to be the most sensitive and specific method for HSA detection. Principle of the assay is depending on the affinity binding of HSA and antibody. The final products could be measured by detection of the turbidity, fluorescence intensity and UV absorption (Basil, *Clinica Chimica*, Vol. 258, 1997, 3-20). In order to get an accurate results, the assay requires several sample dilutions, leading to high cost and time consuming. However, this assay is suitable for detection of low HSA concentration in urine and other secretions.

Glycated Human Serum Albumin Detection

Nowadays, glycated human serum albumin detection is based on the binding of boronic acid and cis-diol group of the glucose molecule on the GHSA protein. The most three popular methods are described below.

1. Boronate Affinity Chromatography (BAC): Boronic acids, which are coated on the resin beads, will bind to glucose molecule on GHSA protein in the sample. Then the unbound molecules will be washed out and the remaining GHSA protein will be analyzed by measuring the absorption of tryptophan amino acids.

2. Enzyme Link Boronate Immunoassay (ELIBA): Antibodies against HSA protein will bind to both HSA and GHSA protein. After the binding of Horseradish Peroxidase (HPR) conjugated boronic molecule and cis-diol group on the GHSA protein, GHSA concentration can be analyzed using the similar method as ELISA (Ikeda, *Clinical Chemistry*, Vol. 44, No. 2, 1998, 256-263).

3. Enzymatic Assay: Amino acids with the glucose attachment will be digested by proteinase enzyme, resulting in single glycated amino acids. Then glycated amino acids will be oxidized by Ketonamine oxidase enzyme, leading to the formation of hydrogen peroxide. The amount of hydrogen peroxide molecule, which correlated with the concentration of GHSA, can be measured using peroxidase method. On the other hand, total HSA can be analyzed using BCP method as previously described and the percentage of glycation can be calculated (Kohzuma, *Journal of Diabetes Science and Technology*, Vol. 5, No. 6, 1455-1462).

Previous HSA and GHSA detections are suitable for only screening method because they are lacking of specificity. The ideal method should be more specific, which is depending on the affinity binding of the specific binding molecules (antibody or aptamer) and HSA/GHSA.

Aptamers Against Human Serum Albumin and Glycated Human Serum Albumin

Aptamer is a short ssDNA or RNA that specifically bind to target molecule using three-dimensional structure. Target molecules could be cells, proteins, metal ions, and toxin. The aptamer can be selected from the large aptamer library using the method called "Systematic Evolution of Ligands by Exponential Enrichment" or "SELEX" (Tuerk, *Science*, Vol. 249, 1990, 505-510, Ellington, *Nature*, Vol. 346, 1990, 818-822). The principle of the SELEX method is the repeating of aptamers selection against target molecule. The higher pressure condition will be added to each selection process to obtain higher specific binding aptamers. Then the selected aptamers will be amplified and the process will be repeated until the affinity binding of selected aptamer is constant.

Aptamer is similar as antibody, in which they can bind specifically to target molecule. However, aptamer is more stable and easily to produce comparing with the antibody. It has been reported that aptamers could be developed and used as a drug, drug delivery and applied for diagnostic field (Kyung-Mi Song, *Sensors*, Vol. 12, 2012, 612-631). Aptamers against GHSA have been reported in 2007 by Higashimoto and colleagues. They also found that some selected aptamers could inhibit toxicity of GHSA in retinal pericyte (Higashimoto, *Microvascular Research*, 2007, 65-69, US patent number US 2009/0023672 A1).

The present invention is about aptamers against HSA and GHSA. Selected aptamers in this invention have higher binding affinity than that from the previous report and have a potential to be used in the diagnostic field and also drug development.

BRIEF DESCRIPTION OF THE DRAWINGS

FIG. 7: Nucleotide sequences of G8 (SEQ ID NO: 25) and clone 9 (SEQ ID NO: 40) aptamer.

FIG. 8: Binding assay results of G8 aptamer and glycated human serum albumin in comparison with the results of clone 9 aptamer and glycated human serum albumin.

FIG. 9: Graph showing binding affinity of G8 and GHSA comparing with clone 9 and GHSA, which is calculated from FIG. 8.

SUMMARY OF THE INVENTION

Figure 1:
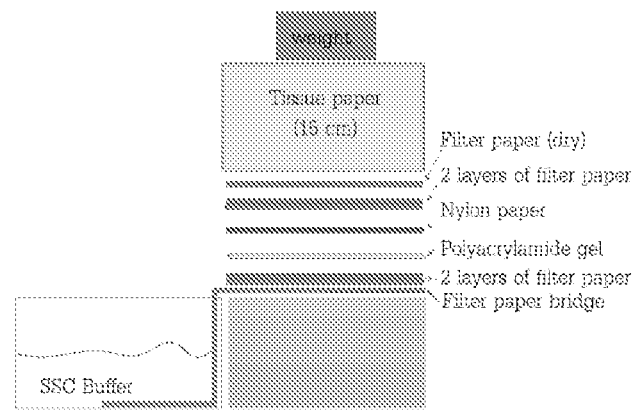
FIG. 1: Transferring of ssDNA aptamer from polyacrylamide gel to nylon membrane.

This invention is about the selection and development of aptamers that specifically bound HSA and GHSA. HSA and GHSA are associated with diabetes mellitus. The length of selected aptamers are around 46-106 bases, in which aptamers against HSA are consisting of 46-106 bases and aptamers against GHSA are consisting of 49-71 bases. All selected aptamers against HSA and GHSA have a potential to be applied for monitoring and drug development of diabetes mellitus and Alzheimer disease. In addition, chemical or fluorescence labeled these aptamers can be used for function and location study of HSA and GHSA.

DETAILED DESCRIPTION OF THE INVENTION

This invention is about aptamer that specifically bound to proteins associated with diabetes mellitus, which are human serum albumin (HSA) and glycated human serum albumin (GHSA). Selected aptamers against HSA and GHSA in this invention are consisting of 46-106 bases and 49-71 bases, respectively. Nucleotide sequences of aptamers are shown in Table 1 and Table 2.

TABLE 1

Nucleotide sequences of aptamers against human serum albumin

| Name | Nucleotide number | Nucleotide sequence | SEQ ID No. |
|---|---|---|---|
| H1 | 88 | AGATTGCACTTACTATCTCCAGGTCTCCCTGAC CACAATAAAAGATAGCGTCCTGCTTGGAATGAA GGGC AATTGAATAAGCTGGTAT | 1 |
| H2 | 88 | AGATTGCACTTACTATCTCCAACACACCCGACC GGGCCCTTATTGCTGACCACCAAACTATGAACA ACGG AATTG AATAAGCTGGTAT | 2 |
| H3 | 46 | AGATTGCACTTACTATCT CCACCCATATG AATTGAATACCCTGGTTT | 3 |
| H4 | 106 | AGATTGCACTTACTATCTATCCCACCACAGAAC CCCAGCCATGCAACCCCACAACAAGACCTCAA CCACC AATTGAATAAGCTGGTAT AATTGAATAAGCTGGTAT | 4 |
| H8 | 87 | ATACCAGCTTATTCAATTCCCCCGGCTTTGGTTT AGAGGTAGTTGCTCATTACTTGTACGCTCCGGA T GAGATAGTAAGTGCAATCT | 5 |
| H10 | 88 | ATACCAGCTTATTCAATTGTTAACCGGTATGTAT AGGATTATGAAAATGCCGCCCATCGACCCTGTT CC GAGATAGTAAGTGCAATCT | 6 |
| H11 | 87 | ATACCAGCTTATTCAATTCCCGTACTGAGGGGG TCCTACCCCGTCTCGGCCCAGCATGTGGTTCGA TG GAGATAGTAAGTGCAATCT | 7 |
| H12 | 106 | AGATTGCACTTACTATCTATCCCACCACAGAAC CCCAGCCATGCAACCCCACAACAAGACCTCAA CCACCAATTGAATAAGCTGGTAT AATTG AATAAGCTGGTAT | 8 |
| H13 | 88 | AGATTGCACTTACTATCTTTGCGCTTGCAGAAC TAGAAACAAACGCGCAACATTATTCGTACACCC CCCC AATTGAATAAGCTGGTAT | 9 |
| H14 | 88 | ATACCAGCTTATTCAATTCGCGCACATATACAGG GCTTTACCAGCGGGGAAGGTTAGCGACGCGAG GGG GAGATAGTAAGTGCAATCT | 10 |
| H16 | 87 | ATACCAGCTTATTCAATTAAGATCCGGATAGCAA TCTGCCGTAGTAGGTCAACGTGTCTGGGGGTT A TAGATAGTAAGTGCAATCT | 11 |
| H17 | 88 | AGATTGCACTTACTATCTCGCGAAGCCAACAAA ATCAACCACCCCACTCTTTAATACATCCCGGGC GCCC AATTGAATAAGCTGGTAT | 12 |
| H18 | 88 | AGATTGCACTTACTATCTCCAAACCACTACACC CTTCTAACCCCCCTGTCTTCCTCGCTCTGACCA CCTT AATTGAATAAGCTGGTAT | 13 |
| H20 | 88 | ATACCAGCTTATTCAATTGTCGTGTCTGGGCCAT TGATGAGTCGTAGTGGGGTTTCGCTCTATCGGG TG TAGATAGTAAGTGCAATCT | 14 |
| H23 | 106 | ATACCAGCTTATTCAATTATACCAGCTTATTCAAT TGTAGAACAATACTCTGGTTAACACTCGTTACA CGTTTATTCCCCTGACACT GAGATAGTAAGTGCAATCT | 15 |
| H24 | 88 | AGATTGCACTTACTATCTATGCCAACATCCCCCC CCTATTCACTAACCATCCTACTAACGTCCTCCGG GT AATTGAATAAGCTGGTAT | 16 |
| H25 | 105 | ATACCAGCTTATTCAATTATACCAGCTTATTCAAT TCGCACTTGTTTAATGCGCAAGTATCTTGGGTG TAGTTGGTCGGTGTGATA GAGATAGTAAGTGCAATCT | 17 |
| H26 | 89 | AGATTGCACTTACTATCTGCACACTACTAAACTA CATATGTCCCCACTCCAACCTACTTGAATCGGG TTC AATTGAATAAGCTGGTATA | 18 |

TABLE 2

Nucleotide sequences of aptamers against glycated human serum albumin

| Name | Nucleotide number | Nucleotide sequence | SEQ ID No. |
|---|---|---|---|
| G1 | 71 | TCTATCCCCCCAGCCTTCCCACTCCAACCCTGC CGGGCCGCTGCATATAACTGAATTGAATAAGCT GGTAT | 19 |
| G2 | 52 | TGGTACATCGACCATCACCGCACCTCACATATT CCGAATTACTCCCGACGTA | 20 |
| G3 | 52 | TACATTGCTCCTGCGGAAAAATTGTCAAACCAT CTACTGCGAAGCGTGTTTT | 21 |
| G4 | 49 | TAGGAGTAGGGGTCGTAGACGGTTGGGCGG AACGGGCGTGGGCATG | 22 |
| G5 | 53 | TGGTACATCGACCATCACCGCACCTCACATATT CCGAATTACTCCCGACGTAT | 23 |
| G7 | 53 | TCGATGGTGGGCAGCCCCAGCACATTCCGTATG TTAACCCCTGCGTTGCCATT | 24 |
| G8 | 49 | GGTGCGGTTCGTGCGGTTGTAGTACTCGTGGCC GATAGAGGTAGTTTCG | 25 |
| G10 | 51 | TCATACTGGGTCATGTACTTAGCTGGTCGCAGC GGGGACTGAGTTAGTGTT | 26 |
| G11 | 53 | TCCCACGCCCGCCCGTCGTTCACCCCTCCCCGC TACCTCCCTATCCAACTGCG | 27 |
| G12 | 53 | TCCCCCCATCACACCCAAGCCGCAGCCACCGA CATAGCAAGCATTGTCTTTCC | 28 |
| G13 | 52 | TCGGGGGGCGTTGATTTTGTTGAAGGGAGGT ATAGTGTCTGTCGGTCTGAT | 29 |
| G14 | 51 | TCCTGCCGAACTCCAAGATCTCCGCTCCGCTCA CGCTGTGTATCCATGGGG | 30 |
| G15 | 53 | TAGTTCTAGGCCGCCCTCGTGATAACCCCCCTC CATCTTCCCTACGATGTACT | 31 |
| G17 | 52 | TGGGTCATCGTCGTCTTAGGCGCGTGAAAGGG GTAGGATGGCGGGTAGGATG | 32 |
| G19 | 52 | TGCAAGGTGGGCATTGGCATTGCGTAGCTAGGG GGTGAAGGCGTGTGGTTTT | 33 |
| G23 | 71 | TCAGGCAAACACAATATACGCAATATCACGGTG GAATTTCAAGGCCTTTCATCAATTGAATAAGCT GGTAT | 34 |
| G24 | 53 | TCAAAAGCGCGCTAAGCCTAGTTCGACAACTT CACCAACGACCCACTATTCGT | 35 |
| G25 | 51 | TCCCTAACCCGCTCTAACCAACCGCGCTCAGTC CGACATCCGTAAACGGGC | 36 |
| G26 | 53 | TCCAACCCAGACCAACATTCCTCGCCTCCGCTA TCTGCACCGCCACACATAAC | 37 |

EXAMPLE 1: QUALITATIVE BINDING ASSAY OF SELECTED APTAMERS AND HSA/GHSA USING ELECTROMOBILITY SHIFT ASSAY (SMSA)

1. Small Scale Preparation of 5' Biotinylated Aptamers
   Step 1: Plasmid DNAs encoding selected aptamer sequences (Table 1 and Table 2) were diluted with sterile water to make 10 nM stock solution for PCR amplification.
   Step 2: Stock solutions from step 1 were used as templates for 50 µL PCR reaction. The PCR reaction is described in Table 3 and 4.

TABLE 3

PCR reaction (50 µL total reaction) for 5' Biotinylated aptamer preparation

| PCR composition | Volume (µL) |
| --- | --- |
| Plasmid DNA encoding aptamer sequence | 1 |
| *25 µM 5' Biotinylated forward primer (5'...Biotin/ATACCAGCTTATTCAATT...3') (SEQ ID NO: 38) | 1 |
| **25 µM 5' Phosphorylated reward primer (5'...Phosphate/AGATTGCACTTACTATCT...3') (SEQ ID NO: 39) | 1 |
| 10 mM dNTP | 1 |
| 10 × Thermo Pol Reaction buffer | 5 |
| Steriled water | 40 |
| 5 U/µL Taq Polymerase | 1 |

Remark:
*5' Biotinylated primer for EMSA analysis
**Phosphorylated primer for λ-Exonuclease digestion

TABLE 4

PCR condition for 5' Biotinylated aptamer preparation

| Step | Process | Temperature | Time |
| --- | --- | --- | --- |
| 1 | Heat | 94° C. | 5 minutes |
| 2 | Denaturation | 94° C. | 1 minutes |
| 3 | Annealing | 36° C. | 30 Seconds |
| 4 | Extension | 72° C. | 30 Seconds |
| 5 | Repeat step 2-4 for 34 rounds | | |
| 6 | Final extension | 72° C. | 10 minutes |
| 7 | Cooling | 4° C. | Until use |

Step 3: 1 µL of 20 U/µL DpnI enzyme was added in the PCR product and incubated at 37° C. for 3 hours. DpnI enzyme will digested plasmid DNA template by cutting at all methyl groups of the plasmid DNA.
Step 4: Then 1 µL λ-Exonuclease enzyme was added in the PCR product and incubated at 37° C. for another 3 hours. Phosphorylated DNA strands will be digested by λ-Exonuclease enzyme.
Step 5: 5' Biotinylated aptamers were purified using QIAquick PCR purification kit (QIAGEN). Then purified aptamers were diluted in 20 µL steriled water. The stock aptamers with concentration around 5-10 ng/µL were stored at −20° C. until use.

2. Binding Assay of Aptamers and Target Proteins (Human Serum Albumin and Glycated Human Serum Albumin) Using Gel Electrophoresis Followed by Southern Blot Analysis
   Step 1: 9 µL of 5' Biotinylated aptamers from previous process with the concentration of 2-10 ng/µL were incubated at 65° C. for 5 minutes to denature secondary structure. After that the reaction was incubated at 4° C. for 1 minutes before use.
   Step 2: 1 µL HSA was mixed with 9 µL of aptamer against HSA and 1 µL of 0.4 µg/µL GHSA was mixed with 9 µL of aptamer against GHSA.
   Step 3: The reaction from step 2 was incubated at 25° C. for 1 hour and analyzed on 8% polyacrylamide gel at 100 V for 30 minutes.
   Step 4: Aptamers on the polyacrylamide gel from step 3 were transferred to nylon membrane (Amersham Hybond-N+; GE Healthcare). Classical DNA/RNA transferring method was used. The transferring buffer was SSC (150 mM $CaCl_2$ and 15 mM Sodium citrate, pH 7.0) and incubation time was 12 h. The schematic of transferring set up is shown in FIG. 1.
   Step 5: Aptamer analysis using Phototope®-Star Detection Kit (New England Biolabs)
      Nylon membrane was removed from the transferring set up and put in the clear plastic container containing solution A (5% Sodium Dodecyl Sulfate (SDS), 125 mM NaCl, 25 mM Sodium Phosphate, pH 7.5). The system was incubated at room temperature for 5 minutes with gentle shaking.
      The solution was discarded and 10 µL of streptavidin in 20 mL of solution A was added in the reaction container and incubated at room temperature for 5 minutes with gentle shaking.
      The solution was discarded. Then the membrane was washed 3 times by using solution B (1:10 of solution A in steriled water) with gentle shaking for 5 min. Then the washing buffer was discarded before the next round washing.
      µL of Biotinylated alkaline phosphatase in 20 mL of solution A was added in the container. Then the system was incubated at room temperature for 5 minutes with gentle shaking. Then the solution is discarded.
      The membrane was washed 3 times by solution C (10 mM Tris HCl, 10 mM NaCl, 1 mM $Mg_2Cl$, pH 9.50) with gentle shaking and then solution is discarded.
      CDP star was added on the membrane (until solution covered the membrane) and incubated at room temperature (dark) for 10 minutes with gentle shaking.
      The nylon membrane was attached to the x-ray film in the film cassette for 1 minutes (dark room).
      The x-ray film was removed from the cassette and dipped in developer solution until the aptamer band was appeared on the x-ray film.
      The x-ray film was washed with clean water for 30 seconds, followed by soaking in fixer solution until the x-ray film was clear.
      The x-ray film was washed in clean water for 30 seconds and air dried. Remark: Steps involved the x-ray film were perfoimed in the dark room.
      Density of the aptamer band on the dried x-ray film was analyzed and the positive results were shown in Table 5 and Table 6.

TABLE 5

Aptamers bound human serum albumin with EMSA positive result

| Name | Nucleotide number | Nucleotide sequence | SEQ ID No. |
| --- | --- | --- | --- |
| H8 | 87 | ATACCAGCTTATTCAATTCCCCCGGCTTTGG TTTAGAGGTAGTTGCTCATTACTTGTACGCT CCGGAT GAGATAGTAAGTGCAATCT | 5 |

TABLE 5 -continued

Aptamers bound human serum albumin with EMSA positive result

| Name | Nucleotide number | Nucleotide sequence | SEQ ID No. |
|---|---|---|---|
| H14 | 88 | ATACCAGCTTATTCAATTCGCGCACATATAC AGGGCTTTACCAGCGGGGAAGGTTAGCGA CGCGAGGGG GAGATAGTAAGTGCAATCT | 10 |
| H17 | 88 | AGATTGCACTTACTATCTCGCGAAGCCAAC AAAATCAACCACCCCACTCTTTAATACATC CCGGGCGCCC AATTGAATAAGCTGGTAT | 12 |

TABLE 6

Aptamers bound glycated human serum albumin with EMSA positive result

| Name | Nucleotide number | Nucleotide sequence | SEQ ID No |
|---|---|---|---|
| G1 | 71 | TCTATCCCCCCAGCCTTCCCACTCCAACCCT GCCGGGCCGCTGCATATAACTGAATTGAATA AGCTGGTAT | 19 |
| G8 | 49 | GGTGCGGTTCGTGCGGTTGTAGTACTCGTG GCCGATAGAGGTAGTTTCG | 25 |
| G10 | 51 | TCATACTGGGTCATGTACTTAGCTGGTCGCA GCGGGGACTGAGTTAGTGTT | 26 |
| G12 | 53 | TCCCCCCATCACACCCAAGCCGCAGCCACC GACATAGCAAGCATTGTCTTTCC | 28 |
| G15 | 53 | TAGTTCTAGGCCGCCCTCGTGATAACCCCCC TCCATCTTCCCTACGATGTACT | 31 |

EXAMPLE 2: THERMODYNAMIC PROPERTIES OF SELECTED APTAMERS

Aptamer usually binds to the target molecule using secondary structure folding, therefore thermodynamic properties of selected aptamers (Table 5 and Table 6) were characterized by using MFold program, which is free software and developed by Michael Zuker and Nick Markham from College of Arts and Sciences, State University of New York at Albany, USA (http://mfold.rna.albany.edu/?q=mfold/DNA-Folding-Form). Parameters used in this study were shown here and the result is shown in Table 7 and Table 8.
Linear ssDNA
Temperature at 25° C.
0.1 M $Mg^{2+}$ concentration
5% Suboptimality number
Upper bound on the number of computed folding at 50

TABLE 7

Thermodynamic properties of aptamers against human serum albumin

| Name | Secondary structure number | ΔG (kcal/mol) | ΔH (kcal/mol) | ΔS (cal/(K · mol)) | Tm (° C.) |
|---|---|---|---|---|---|
| H8 | 1 | −10.47 | −166.60 | −523.6 | 44.9 |
|  | 2 | −10.18 | −149.00 | −465.6 | 46.8 |
|  | 3 | −9.97 | −138.10 | −429.7 | 48.1 |
|  | 4 | −9.77 | −151.50 | −475.3 | 45.5 |

TABLE 7-continued

Thermodynamic properties of aptamers against human serum albumin

| Name | Secondary structure number | ΔG (kcal/mol) | ΔH (kcal/mol) | ΔS (cal/(K · mol)) | Tm (° C.) |
|---|---|---|---|---|---|
| H14 | 1 | −8.69 | −103.10 | −316.6 | 52.4 |
|  | 2 | −8.10 | −91.00 | −278 | 54.1 |
|  | 3 | −7.99 | −112.80 | −351.5 | 47.7 |
|  | 4 | −7.84 | −116.70 | −365.1 | 46.4 |
|  | 5 | −7.81 | −108.10 | −336.3 | 48.2 |
| H17 | 1 | −5.41 | −105.10 | −334.3 | 41.1 |
|  | 2 | −4.98 | −111.40 | −356.9 | 38.9 |

TABLE 8

Thermodynamic properties of aptamer against glycated human serum albumin

| Name | Secondary structure number | ΔG (kcal/mol) | ΔH (kcal/mol) | ΔS (cal/(K · mol)) | Tm (° C.) |
|---|---|---|---|---|---|
| G1 | 1 | −5.59 | −90.10 | −283.4 | 44.7 |
|  | 2 | −5.56 | −88.50 | −278.1 | 44.9 |
|  | 3 | −5.36 | −82.60 | −259 | 45.6 |
|  | 4 | −4.63 | −69.80 | −218.5 | 46.1 |
| G8 | 1 | −4.09 | −45.10 | −137.5 | 54.7 |
|  | 2 | −3.86 | −52.30 | −162.4 | 48.7 |
|  | 3 | −3.43 | −45.90 | −142.4 | 49 |
|  | 4 | −3.28 | −53.30 | −167.7 | 44.5 |
|  | 5 | −3.23 | −60.90 | −193.4 | 41.6 |
|  | 6 | −3.17 | −61.20 | −194.6 | 41.2 |
| G10 | 1 | −8.16 | −81.00 | −244.3 | 58.4 |
| G12 | 1 | −3.68 | −55.20 | −172.7 | 46.2 |
|  | 2 | −3.05 | −43.20 | −134.6 | 47.6 |
| G15 | 1 | −5.41 | −77.30 | −241.1 | 47.4 |

Figure 2:
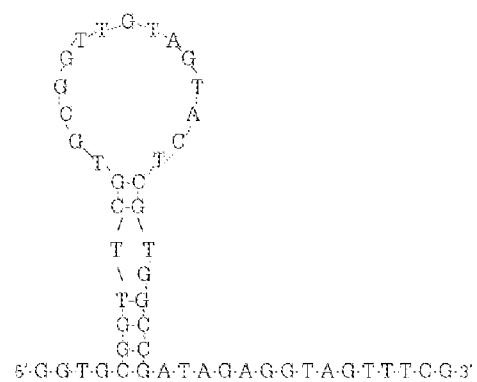
FIG. 2: Predicted secondary structure of aptamer G8 (SEQ ID NO: 25) (MFold program).

The result shows that ΔG of selected aptamers were between −10.47 kcal/mol and −3.05 kcal/mol. The melting temperature (temperature at 50% aptamer structure is denatured) was 38.9-58.4° C. To maintain secondary structure formation, experiments involved these aptamers should be performed at lower temperature than 38.9° C. The secondary structure of G8 aptamer is shown in FIG. 2.

EXAMPLE 3: SEMI-QUANTITATIVE BINDING ASSAY OF SELECTED APTAMERS

Figure 3:
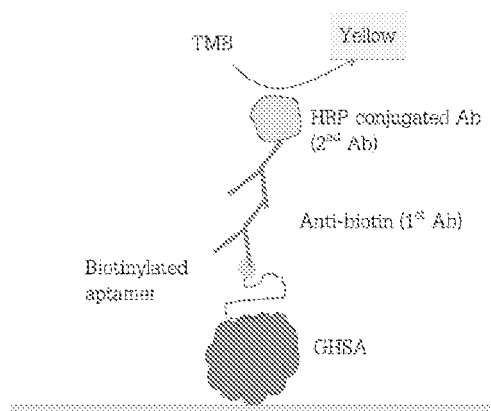
FIG. 3: The schematic showing indirect ELISA using aptamer.

The binding assay of selected aptamers against HSA and aptamers against GHSA is deteimined by using Indirect Enzyme-Linked Immunosorbent Assay (Indirect ELISA) and Direct Enzyme-Linked Immunosorbent Assay (Direct ELISA), as described below.
3.1. Indirect Enzyme-Linked Immunosorbent Assay (Indirect ELISA)
The principle of this experiment is based on two antibodies, which are antibodies against 5' biotinylated aptamer and antibodies against the first antibody. The second antibody is conjugated with horseradish peroxidase enzyme (HRP), which can changes TMB color from blue to be yellow. The yellow color intensity is direct indicator for the target protein concentration. Schematic of the Indirect ELISA is shown in FIG. 3. Random selected aptamers in Table 5 and Table 6 were chosen for analysis using this method.
Indirect ELISA Protocol
Step 1: 0.8 μg of BSA or HSA or GHSA was added in 50 μl of 0.05 M carbonate buffer in 96 well plate (50 μL/well) and incubated at 4° C. for 1 night. In this process, all proteins will be coated on the 96 well plate.

Step 2: The reaction from step 1 was washed 5 times with Phosphate buffer (PBST) (0.05% Tween) using ELISA washing machine (Fluido 2) and tapped for 3-5 times.

Step 3: 200 μL of blocking solution (PBST with 1% Tryptone) was added in the reaction and incubated at room temperature for 1 hour, then washed 5 times with PBST using Fluido 2 and tapped for 3-5 times.

Step 4: 1 μL of varied concentrations of 5' Biotinylate aptamer (200, 20, 2 and 0.2 ng/μL) diluted in 50 μL PBST buffer were added in the reaction. After incubating at room temperature for 1 hour, the reaction was washed with PBST for 5 times using Fluido2 and tapped for 3-5 times.

Step 5: 50 μL of anti-biotin (1$^{st}$ antibody) with the dilution of 1:3840 in PBST was added in the reaction. After incubating at room temperature for 30 minutes, the reaction was washed with PBST for 5 times using Fluido2 and tapped for 3-5 times.

Step 6: 50 μL of anti-biotin antibody conjugated with HRP (2$^{nd}$ antibody) with the dilution of 1:10,000 was added in the reaction. After incubating at room temperature for 30 minutes, the reaction was washed with PBST for 5 times using Fluido2 and tapped for 3-5 times.

Step 7: 50 μL of TMB (HRP substrate) was added in the reaction. Then the reaction was incubated at room temperature (dark) for 30 minutes.

Step 8: 50 μL of 0.6 M $H_2SO_4$ was added in the reaction and immediately measured the $OD_{450\ nm}$ using spectrophotometer.

The indirect ELISA result showed the positive results from G12 and H14 aptamer and more positive comparing with clone 9, which is the positive control aptamer from the previous study. These results indicated that selected aptamers from this invention bound GHSA tighter than that from the other study. The indirect ELISA result is shown in Table 9.

TABLE 9

Binding assay of aptamers against human serum albumin and glycated human serum albumin using Indirect ELISA.

| Aptamer name | Concentration (nM) | Indirect ELISA with HSA | Indirect ELISA with GHSA |
|---|---|---|---|
| Clone 9 | 200 | + | + |
|  | 20 | − | + |
|  | 2 | + | + |
|  | 0.2 | + | − |
| G12 | 200 | − | − |
|  | 20 | − | − |
|  | 2 | − | + |
|  | 0.2 | − | − |
| H14 | 200 | + | − |
|  | 20 | + | − |
|  | 2 | + | − |
|  | 0.2 | + | − |

3.2 Direct Enzyme-Linked Immunosorbent Assay (Direct ELISA)

Figure 4:
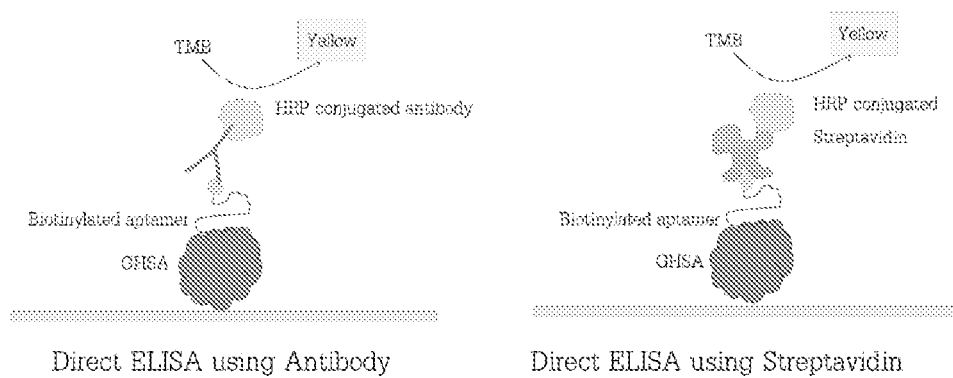
FIG. 4: The schematic showing direct ELISA using antibody (left) and streptavidin (right).

Direct ELISA was used for study the binding of the selected aptamer and HSA or GHSA. G8 aptamer was chosen to be a model for direct ELISA. The strategy is based on antibody or streptavidin conjugated HRP, which can change the TMB color from blue to be yellow. Color intensity is depending on concentration of aptamer bound human serum albumin. Short explanation of direct ELISA (based on antibody conjugated HRP and streptavidin conjugated HRP) is shown in FIG. 4. G8 aptamer was chosen to be a model for this study.

Direct ELISA Protocol

Step 1: 1 μg proteins (Lysozyme, BSA, HSA or GHSA) in 50 μL of 0.05 M Carbonate Buffer were coated on 96-well plat and incubated at 4° C. overnight.

Step 2: The reaction was washed with PBST (0.5% Tween) for 5 times ELISA washing machine (Fluido 2) and tapped for 3-5 times.

Step 3: The reaction was incubated with 200 μL of 2% Tryptone in PBST at room temperature for 1 hour, then washed with PBST for 5 times and tapped for 3-5 times.

Step 4: 50 μL of 40 ng aptamer in PBST (1% Tryptone) was added in the reaction and incubated at room temperature for 1 hour then washing 5 times with PBST and tapped for 3-5 times.

Step 5:

In case of direct ELISA using antibody, 50 μL of antibody in PBST (1% Tryptone) with dilution of 1:1000, 1:2000, 1:3000 and 1:4000 were added in the reaction.

In case of direct ELISA using streptavidin, 50 μL of streptavidin in PBST (1% Tryptone) with dilution of 1:1000, 1:2000, 1:3000 and 1:4000 were added in the reaction.

Then the reaction was incubated at room temperature for 1 hour before washing 5 times with PBST and tapped for 3-5 times.

Step 6: 50 μL of TMB was added in the reaction and incubated at room temperature for 30 minutes.

Step 7: The reaction was stopped by adding 50 μL of 0.6 M $H_2SO_4$ and measured OD450 nm by using spectrophotometer.

Step 8: Results from direct ELISA using antibody and streptavidin were compared and the best dilution of antibody and streptavidin was chosen for future study.

Figure 5:
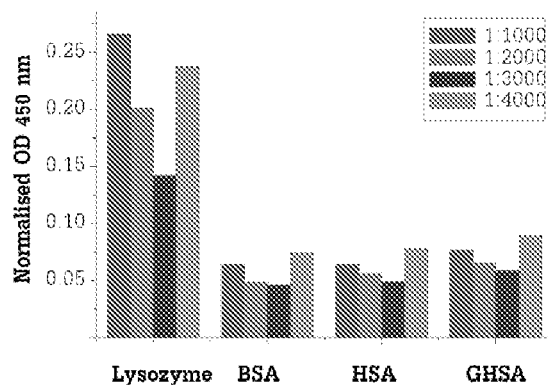
FIG. 5: Graph shows the binding affinity of G8 aptamer and human serum albumin using direct ELISA and antibody dilutions 1:1000, 1:2000, 1:3000 and 1:4000.
Figure 6:
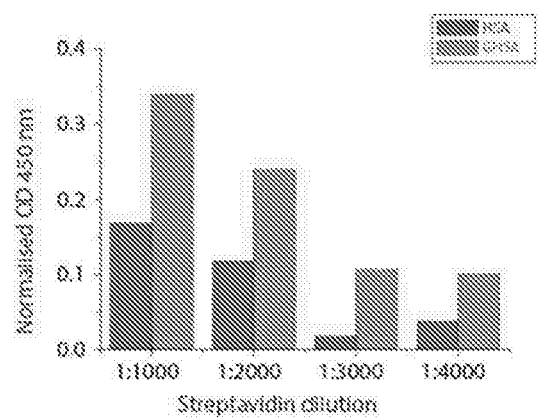
FIG. 6: Graph shows the binding affinity of G8 aptamer and glycated human serum albumin using direct ELISA and streptavidin dilutions 1:1000, 1:2000, 1:3000 and 1:4000.

The result from direct ELISA using antibody showed similar OD450 from all proteins (Lysozyme, BSA, HSA and GHSA) indicating that either G8 aptamer or antibody was non-specific binding to proteins from all dilutions (1:1000, 1:2000, 1:3000 and 1:4000) as shown in FIG. 5. On the other hand, the result from direct ELISA using streptavidin showed that OD450 from GHSA is significant higher (5 times) than that from HSA (Streptavidin dilution 1:3000). The later result indicated that G8 aptamer specifically bound GHSA (FIG. 6).

EXAMPLE 4: QUANTITATIVE BINDING STUDY OF G8 APTAMER AND GLYCATED HUMAN SERUM ALBUMIN

The quantitative binding of G8 aptamer from this invention and clone 9 aptamer from the previous study were analyzed by electromobility shifted assay (EMSA) and results were compared. The EMSA protocol was described in the previous section. 4 ng of 5' Biotinylated DNA aptamers (G8 and clone 9 sequences is shown in FIG. 7) were incubated with varied amounts of glycated human serum albumin as shown below.

(1) 0 ng
(2) 0.0125 ng
(3) 0.025 ng
(4) 0.05 ng
(5) 0.1 ng
(6) 0.2 ng
(7) 0.4 ng

For the control experiment, selected aptamer was incubate with/without 0.4 μg human serum albumin at 25° C. for 1 hour, then samples were analyzed by electrophoresis following by southern blot analysis (similar as Example 1). The result is shown in FIG. 8.

The density of shifted band, which is the binding of aptamer and GHSA, was analyzed using AlphaImager HP. Fraction of bound aptamer (Fa) and dissociation constant (Kd) were calculated using equations below.

$$Fa=[T]/(Ka+[T]) \text{ and } Kd=1/Ka(\text{At the optimal aptamer concentration}, Kd=0.5Fa)$$

Fa=aptamer concentration

[T]=GHSA concentration

Ka=Association constant, which is optimal GHSA concentration that bind to optimal aptamer concentration.

Kd=Dissociation Constant, which is an affinity binding of GHSA and aptamer (1/Ka)

The result showed that G8 aptamer bound GHSA with the Kd of 0.08±0.1 µmole, which is higher affinity comparing with the binding of clone 9 and GHSA, as shown in FIG. 9. Therefore, selected aptamers against HSA and GHSA from this invention has a potential for development of HSA and GHSA analysis in other secretions and drug development in the diabetic retinopathy and also drug delivery.

BEST MODE FOR CARRYING OUT THE INVENTION

Previously described in "DETAILED DESCRIPTION OF THE INVENTION" section.

INDUSTRIAL APPLICABILITY

1. Human serum albumin (HSA) is normally found in human serum and urine. In case of abnormal liver functions, higher amount of HSA will be found from serum and urine. Therefore, aptamers specifically bound HSA can be potentially developed for analysis of HSA in both serum and urine.
2. Glycated human serum albumin (GHSA) can be highly produced within 2-3 weeks in diabetes mellitus patience. Therefore, aptamers specifically bound GHSA can be applied for an analysis of diabetes mellitus in combination with HbA1 c level.
3. Selected aptamers in this invention could bind to HSA or GHSA. Therefore, these aptamers have a potential to be a drug for treatment of diabetes mellitus and abnormal liver functions.
4. Chemical or fluorescence labeled selected aptamers can be potentially used for study the binding position on the HSA or GHSA protein.

---

The invention claimed is:

1. An aptamer that specifically binds to HSA or GHSA, said aptamer comprising a single-stranded DNA with a length of 46-106 bases, wherein the aptamer comprises a sequence selected from the group consisting of SEQ ID NOs: 1 to 37.

2. The aptamer of claim 1, wherein the aptamer specifically binds to HSA.

3. The aptamer of claim 1, wherein the aptamer specifically binds to GHSA and wherein the length of the single-stranded DNA is 49-71 bases.

4. A kit for analyzing HSA and GHSA comprising the aptamer of claim 1.

5. The aptamer of claim 3, wherein the aptamer comprises a sequence selected from the group consisting of SEQ ID NOs: 19 to 37.

6. The aptamer of claim 1, wherein the aptamer further comprises biotin.

7. The aptamer of claim 1, wherein the aptamer further comprises a fluorescent label.

8. A method of detecting HSA or GHSA, comprising
contacting a sample with the aptamer of claim 1, wherein the aptamer further comprises a detectable marker; and
detecting the presence or absence of aptamer bound to HSA or GHSA.

9. The method of claim 8, wherein the aptamer specifically binds to HSA.

10. The method of claim 8, wherein the aptamer specifically binds to GHSA and wherein a length of the single-stranded DNA is 49-71 bases.

11. The method of claim 8, wherein the detectable marker comprises biotin or a fluorescent label.

12. The method of claim 8, wherein the detectable marker comprises biotin and the step of detecting the aptamer bound to HSA or GHSA comprises contacting the biotin with an antibody or antigen binding fragment thereof that specifically binds to the biotin.

13. The method of claim 8, wherein the detectable marker comprises biotin and the step of detecting the aptamer bound to HSA or GHSA comprises contacting the biotin with a streptavidin that specifically binds to the biotin.

14. The method of claim 8, wherein detecting the aptamer bound to HSA or GHSA further comprises quantifying the amount of aptamer bound to HSA or GHSA.

* * * * *

SEQUENCE LISTING

```
<160> NUMBER OF SEQ ID NOS: 40

<210> SEQ ID NO 1
<211> LENGTH: 88
<212> TYPE: DNA
<213> ORGANISM: Artificial Sequence
<220> FEATURE:
<223> OTHER INFORMATION: Aptamer against HSA H1

<400> SEQUENCE: 1
agattgcact tactatctcc aggtctccct gaccacaata aaagatagcg tcctgcttgg     60
aatgaagggc aattgaataa gctggtat                                         88

<210> SEQ ID NO 2
<211> LENGTH: 88
<212> TYPE: DNA
<213> ORGANISM: Artificial Sequence
<220> FEATURE:
<223> OTHER INFORMATION: Aptamer against HSA H2

<400> SEQUENCE: 2
agattgcact tactatctcc aacacacccg accgggccct tattgctgac caccaaacta     60
tgaacaacgg aattgaataa gctggtat                                         88

<210> SEQ ID NO 3
<211> LENGTH: 47
<212> TYPE: DNA
<213> ORGANISM: Artificial Sequence
<220> FEATURE:
<223> OTHER INFORMATION: Aptamer against HSA H3

<400> SEQUENCE: 3
agattgcact tactatctcc acccatatga attgaatacc ctggttt                    47

<210> SEQ ID NO 4
<211> LENGTH: 106
<212> TYPE: DNA
<213> ORGANISM: Artificial Sequence
```

```
<220> FEATURE:
<223> OTHER INFORMATION: Aptamer against HSA H4

<400> SEQUENCE: 4
agattgcact tactatctat cccaccacag aaccccagcc atgcaacccc acaacaagac      60
ctcaaccacc aattgaataa gctggtataa ttgaataagc tggtat                   106

<210> SEQ ID NO 5
<211> LENGTH: 87
<212> TYPE: DNA
<213> ORGANISM: Artificial Sequence
<220> FEATURE:
<223> OTHER INFORMATION: Aptamer against HSA H8

<400> SEQUENCE: 5
ataccagctt attcaattcc cccggctttg gtttagaggt agttgctcat tacttgtacg      60
ctccggatga gatagtaagt gcaatct                                         87

<210> SEQ ID NO 6
<211> LENGTH: 88
<212> TYPE: DNA
<213> ORGANISM: Artificial Sequence
<220> FEATURE:
<223> OTHER INFORMATION: Aptamer against HSA H10

<400> SEQUENCE: 6
ataccagctt attcaattgt taaccggtat gtataggatt atgaaaatgc cgcccatcga      60
ccctgttccg agatagtaag tgcaatct                                        88

<210> SEQ ID NO 7
<211> LENGTH: 87
<212> TYPE: DNA
<213> ORGANISM: Artificial Sequence
<220> FEATURE:
<223> OTHER INFORMATION: Aptamer against HSA H11

<400> SEQUENCE: 7
ataccagctt attcaattcc cgtactgagg gggtcctacc ccgtctcggc ccagcatgtg      60
gttcgatgga gatagtaagt gcaatct                                         87

<210> SEQ ID NO 8
<211> LENGTH: 106
<212> TYPE: DNA
<213> ORGANISM: Artificial Sequence
<220> FEATURE:
<223> OTHER INFORMATION: Aptamer against HSA H12

<400> SEQUENCE: 8
agattgcact tactatctat cccaccacag aaccccagcc atgcaacccc acaacaagac      60
ctcaaccacc aattgaataa gctggtataa ttgaataagc tggtat                   106

<210> SEQ ID NO 9
<211> LENGTH: 88
<212> TYPE: DNA
<213> ORGANISM: Artificial Sequence
<220> FEATURE:
<223> OTHER INFORMATION: Aptamer against HSA H13

<400> SEQUENCE: 9
agattgcact tactatcttt gcgcttgcag aactagaaac aaacgcgcaa cattattcgt      60
acaccccccc aattgaataa gctggtat                                        88
```

<210> SEQ ID NO 10
<211> LENGTH: 88
<212> TYPE: DNA
<213> ORGANISM: Artificial Sequence
<220> FEATURE:
<223> OTHER INFORMATION: Aptamer against HSA H14

<400> SEQUENCE: 10
ataccagctt attcaattcg cgcacatata cagggcttta ccagcgggga aggttagcga    60
cgcgaggggg agatagtaag tgcaatct                                       88

<210> SEQ ID NO 11
<211> LENGTH: 87
<212> TYPE: DNA
<213> ORGANISM: Artificial Sequence
<220> FEATURE:
<223> OTHER INFORMATION: Aptamer against HSA H16

<400> SEQUENCE: 11
ataccagctt attcaattaa gatccggata gcaatctgcc gtagtaggtc aacgtgtctg    60
gggggttata gatagtaagt gcaatct                                        87

<210> SEQ ID NO 12
<211> LENGTH: 88
<212> TYPE: DNA
<213> ORGANISM: Artificial Sequence
<220> FEATURE:
<223> OTHER INFORMATION: Aptamer against HSA H17

<400> SEQUENCE: 12
agattgcact tactatctcg cgaagccaac aaaatcaacc accccactct ttaatacatc    60
ccgggcgccc aattgaataa gctggtat                                       88

<210> SEQ ID NO 13
<211> LENGTH: 88
<212> TYPE: DNA
<213> ORGANISM: Artificial Sequence
<220> FEATURE:
<223> OTHER INFORMATION: Aptamer against HSA H18

<400> SEQUENCE: 13
agattgcact tactatctcc aaaccactac acccttctaa cccccctgtc ttcctcgctc    60
tgaccacctt aattgaataa gctggtat                                       88

<210> SEQ ID NO 14
<211> LENGTH: 88
<212> TYPE: DNA
<213> ORGANISM: Artificial Sequence
<220> FEATURE:
<223> OTHER INFORMATION: Aptamer against HSA H20

<400> SEQUENCE: 14
ataccagctt attcaattgt cgtgtctggg ccattgatga gtcgtagtgg ggtttcgctc    60
tatcgggtgt agatagtaag tgcaatct                                       88

<210> SEQ ID NO 15
<211> LENGTH: 106
<212> TYPE: DNA
<213> ORGANISM: Artificial Sequence
<220> FEATURE:
<223> OTHER INFORMATION: Aptamer against HSA H23

<400> SEQUENCE: 15

```
ataccagctt attcaattat accagcttat tcaattgtag aacaatactc tggttaacac      60
tcgttacacg tttattcccc tgacactgag atagtaagtg caatct                   106
```

<210> SEQ ID NO 16
<211> LENGTH: 88
<212> TYPE: DNA
<213> ORGANISM: Artificial Sequence
<220> FEATURE:
<223> OTHER INFORMATION: Aptamer against HSA H24

<400> SEQUENCE: 16

```
agattgcact tactatctat gccaacatcc cccccctatt cactaaccat cctactaacg      60
tcctccgggt aattgaataa gctggtat                                        88
```

<210> SEQ ID NO 17
<211> LENGTH: 105
<212> TYPE: DNA
<213> ORGANISM: Artificial Sequence
<220> FEATURE:
<223> OTHER INFORMATION: Aptamer against HSA H25

<400> SEQUENCE: 17

```
ataccagctt attcaattat accagcttat tcaattcgca cttgtttaat gcgcaagtat      60
cttgggtgta gttggtcggt gtatagaga tagtaagtgc aatct                     105
```

<210> SEQ ID NO 18
<211> LENGTH: 89
<212> TYPE: DNA
<213> ORGANISM: Artificial Sequence
<220> FEATURE:
<223> OTHER INFORMATION: Aptamer against HSA H26

<400> SEQUENCE: 18

```
agattgcact tactatctgc acactactaa actacatatg tccccactcc aacctacttg      60
aatcgggttc aattgaataa gctggtata                                       89
```

<210> SEQ ID NO 19
<211> LENGTH: 71
<212> TYPE: DNA
<213> ORGANISM: Artificial Sequence
<220> FEATURE:
<223> OTHER INFORMATION: Aptamer against GHSA G1

<400> SEQUENCE: 19

```
tctatccccc cagccttccc actccaaccc tgccgggccg ctgcatataa ctgaattgaa      60
taagctggta t                                                          71
```

<210> SEQ ID NO 20
<211> LENGTH: 52
<212> TYPE: DNA
<213> ORGANISM: Artificial Sequence
<220> FEATURE:
<223> OTHER INFORMATION: Aptamer against GHSA G2

<400> SEQUENCE: 20

```
tggtacatcg accatcaccg cacctcacat attccgaatt actcccgacg ta              52
```

<210> SEQ ID NO 21
<211> LENGTH: 52
<212> TYPE: DNA
<213> ORGANISM: Artificial Sequence
<220> FEATURE:

<223> OTHER INFORMATION: Aptamer against GHSA G3

<400> SEQUENCE: 21
tacattgctc ctgcggaaaa attgtcaaac catctactgc gaagcgtgtt tt          52

<210> SEQ ID NO 22
<211> LENGTH: 49
<212> TYPE: DNA
<213> ORGANISM: Artificial Sequence
<220> FEATURE:
<223> OTHER INFORMATION: Aptamer against GHSA G4

<400> SEQUENCE: 22
taggagtagg gggtcgtaga cggttggggc ggaacgggcg tggggcatg              49

<210> SEQ ID NO 23
<211> LENGTH: 53
<212> TYPE: DNA
<213> ORGANISM: Artificial Sequence
<220> FEATURE:
<223> OTHER INFORMATION: Aptamer against GHSA G5

<400> SEQUENCE: 23
tggtacatcg accatcaccg cacctcacat attccgaatt actcccgacg tat         53

<210> SEQ ID NO 24
<211> LENGTH: 53
<212> TYPE: DNA
<213> ORGANISM: Artificial Sequence
<220> FEATURE:
<223> OTHER INFORMATION: Aptamer against GHSA G7

<400> SEQUENCE: 24
tcgatggtgg gcagccccag cacattccgt atgttaaccc ctgcgttgcc att         53

<210> SEQ ID NO 25
<211> LENGTH: 49
<212> TYPE: DNA
<213> ORGANISM: Artificial Sequence
<220> FEATURE:
<223> OTHER INFORMATION: Aptamer against GHSA G8

<400> SEQUENCE: 25
ggtgcggttc gtgcggttgt agtactcgtg gccgatagag gtagtttcg              49

<210> SEQ ID NO 26
<211> LENGTH: 51
<212> TYPE: DNA
<213> ORGANISM: Artificial Sequence
<220> FEATURE:
<223> OTHER INFORMATION: Aptamer against GHSA G10

<400> SEQUENCE: 26
tcatactggg tcatgtactt agctggtcgc agcggggact gagttagtgt t           51

<210> SEQ ID NO 27
<211> LENGTH: 53
<212> TYPE: DNA
<213> ORGANISM: Artificial Sequence
<220> FEATURE:
<223> OTHER INFORMATION: Aptamer against GHSA G11

<400> SEQUENCE: 27
tcccacgccc gcccgtcgtt cacccctccc cgctacctcc ctatccaact gcg         53

```
<210> SEQ ID NO 28
<211> LENGTH: 53
<212> TYPE: DNA
<213> ORGANISM: Artificial Sequence
<220> FEATURE:
<223> OTHER INFORMATION: Aptamer against GHSA G12

<400> SEQUENCE: 28 tcccccatc acacccaagc cgcagccacc gacatagcaa gcattgtctt tcc          53

<210> SEQ ID NO 29
<211> LENGTH: 52
<212> TYPE: DNA
<213> ORGANISM: Artificial Sequence
<220> FEATURE:
<223> OTHER INFORMATION: Aptamer against GHSA G13

<400> SEQUENCE: 29
tcgggggggc gttgattttg ttgaagggag gtatagtgtc tgtcggtctg at           52

<210> SEQ ID NO 30
<211> LENGTH: 51
<212> TYPE: DNA
<213> ORGANISM: Artificial Sequence
<220> FEATURE:
<223> OTHER INFORMATION: Aptamer against GHSA G14

<400> SEQUENCE: 30
tcctgccgaa ctccaagatc tccgctccgc tcacgctgtg tatccatggg g            51

<210> SEQ ID NO 31
<211> LENGTH: 53
<212> TYPE: DNA
<213> ORGANISM: Artificial Sequence
<220> FEATURE:
<223> OTHER INFORMATION: Aptamer against GHSA G15

<400> SEQUENCE: 31
tagttctagg ccgccctcgt gataacccc ctccatcttc cctacgatgt act           53

<210> SEQ ID NO 32
<211> LENGTH: 52
<212> TYPE: DNA
<213> ORGANISM: Artificial Sequence
<220> FEATURE:
<223> OTHER INFORMATION: Aptamer against GHSA G17

<400> SEQUENCE: 32
tgggtcatcg tcgtcttagg cgcgtgaaag gggtaggatg gcgggtagga tg            52

<210> SEQ ID NO 33
<211> LENGTH: 52
<212> TYPE: DNA
<213> ORGANISM: Artificial Sequence
<220> FEATURE:
<223> OTHER INFORMATION: Aptamer against GHSA G19

<400> SEQUENCE: 33
tgcaaggtgg gcattggcat tgcgtagcta gggggtgaag gcgtgtggtt tt            52

<210> SEQ ID NO 34
<211> LENGTH: 71
<212> TYPE: DNA
<213> ORGANISM: Artificial Sequence
<220> FEATURE:
<223> OTHER INFORMATION: Aptamer against GHSA G23
```

```
<400> SEQUENCE: 34
tcaggcaaac acaatatacg caatatcacg gtggaatttc aaggcctttc atcaattgaa    60
taagctggta t                                                         71

<210> SEQ ID NO 35
<211> LENGTH: 53
<212> TYPE: DNA
<213> ORGANISM: Artificial Sequence
<220> FEATURE:
<223> OTHER INFORMATION: Aptamer against GHSA G24

<400> SEQUENCE: 35
tcaaaagcgc gctaagccta gttcgacaac ttcaccaacg acccactatt cgt           53

<210> SEQ ID NO 36
<211> LENGTH: 51
<212> TYPE: DNA
<213> ORGANISM: Artificial Sequence
<220> FEATURE:
<223> OTHER INFORMATION: Aptamer against GHSA G25

<400> SEQUENCE: 36
tccctaaccc gctctaacca accgcgctca gtccgacatc cgtaaacggg c              51

<210> SEQ ID NO 37
<211> LENGTH: 53
<212> TYPE: DNA
<213> ORGANISM: Artificial Sequence
<220> FEATURE:
<223> OTHER INFORMATION: Aptamer against GHSA G26

<400> SEQUENCE: 37
tccaacccag accaacattc ctcgcctccg ctatctgcac cgccacacat aac            53

<210> SEQ ID NO 38
<211> LENGTH: 18
<212> TYPE: DNA
<213> ORGANISM: Artificial Sequence
<220> FEATURE:
<223> OTHER INFORMATION: Biotinylated forward primer

<400> SEQUENCE: 38
ataccagctt attcaatt                                                  18

<210> SEQ ID NO 39
<211> LENGTH: 18
<212> TYPE: DNA
<213> ORGANISM: Artificial Sequence
<220> FEATURE:
<223> OTHER INFORMATION: Phosphorylated reverse primer

<400> SEQUENCE: 39
agattgcact tactatct                                                  18

<210> SEQ ID NO 40
<211> LENGTH: 56
<212> TYPE: DNA
<213> ORGANISM: Artificial Sequence
<220> FEATURE:
<223> OTHER INFORMATION: Clone 9 aptamer

<400> SEQUENCE: 40
taactcactc catactcact tgctgattcg ccaacaacac acccttaaac agtccc        56
```